United States Patent
Bjarnason

(10) Patent No.: US 6,846,485 B2
(45) Date of Patent: Jan. 25, 2005

(54) FISH SERINE PROTEINASE AND THEIR PHARMACEUTICAL AND COSMETIC USE

(76) Inventor: Jon Bragi Bjarnason, Skildinganesi 29, Reykjavik 101 (IS)

( * ) Notice: Subject to any disclaimer, the term of this patent is extended or adjusted under 35 U.S.C. 154(b) by 150 days.

(21) Appl. No.: 10/036,371

(22) Filed: Jan. 7, 2002

(65) Prior Publication Data

US 2002/0141987 A1 Oct. 3, 2002

Related U.S. Application Data

(62) Division of application No. 09/411,688, filed on Oct. 12, 1999.

(30) Foreign Application Priority Data

Jun. 18, 1999  (IS) ................................................ 5086/99

(51) Int. Cl.$^7$ .......................... A61K 38/48; A01N 37/18
(52) U.S. Cl. ......................................... 424/94.64; 514/2
(58) Field of Search .............................. 424/94.1, 94.2, 424/94.64; 514/2

(56) References Cited

U.S. PATENT DOCUMENTS 5,958,406 A * 9/1999 de Faire et al. ......... 424/94.63

6,232,088 B1    5/2001  Franklin et al.

OTHER PUBLICATIONS

Asgeirsson et al., "Purification and characterization of trypsin from the poikilotherm Gadus morhua", *Eur. S. Biochem.* vol. 180, pp 85–94, 1989.

Asgeirsson et al., "Structural and Kinetic Properties of Chymotrypsin from Atlantic Cod (Gadus Morhua). Comparison with Bovine Chymotrypsin", *Comp. Biochem. Pysiol.*, vol. 99B, No. 2, pp. 327–335, 1991.

Asgeirsson et al., "Properties of elastase from Atlantic cod, a cold-adapted proteinase", *Biochimica et Biophysica Acta*, vol. 1164, pp. 91–100, 1993.

Gudmundsdottir et al, "Isolation and characterization of cDNAs from Atlantic cod encoding two different forms of trysinogen", Eur. J. Biochem. vol. 217, 1993, p. 1091–1097.

* cited by examiner

Primary Examiner—Patricia Leith
(74) Attorney, Agent, or Firm—Pillsbury Winthrop LLP

(57) ABSTRACT

Fish derived serine proteinases including trypsins and chymotrypsin derived from cod such as Atlantic cod is used for treating and/or preventing a variety of diseases and disorders such as inflammatory diseases, infectious diseases caused by viruses, bacteria and fungal species and diseases where a receptor binding mechanism is involved in the pathogenesis. Pharmaceutical and cosmetic compositions comprising the proteinases are described.

10 Claims, 4 Drawing Sheets

```
                         SEQUENCE LISTING

<160> NUMBER OF SEQ ID NOS: 8

<210> SEQ ID NO 1
<211> LENGTH: 20
<212> TYPE: PRT
<213> ORGANISM: Gadus sp.
<220> FEATURE:
<221> NAME/KEY: MOD_RES
<222> LOCATION: (6)
<223> OTHER INFORMATION: Q or E
<220> FEATURE:
<221> NAME/KEY: MOD_RES
<222> LOCATION: (8)
<223> OTHER INFORMATION: E or T
<220> FEATURE:
<221> NAME/KEY: MOD_RES
<222> LOCATION: (9)
<223> OTHER INFORMATION: K or R

<400> SEQUENCE: 1

Ile Val Gly Gly Tyr Xaa Cys Xaa Xaa His Ser Gln Ala His Gln Val
 1               5                  10                  15

Ser Leu Asn Ser
            20

<210> SEQ ID NO 2
<211> LENGTH: 20
<212> TYPE: PRT
<213> ORGANISM: Bovine sp.

<400> SEQUENCE: 2

Ile Val Gly Gly Tyr Thr Cys Gly Ala Asn Thr Val Pro Tyr Gln Val
 1               5                  10                  15

Ser Leu Asn Ser
            20

<210> SEQ ID NO 3
<211> LENGTH: 13
<212> TYPE: PRT
<213> ORGANISM: Gadus sp.
<220> FEATURE:
<221> NAME/KEY: MOD_RES
<222> LOCATION: (3)
<223> OTHER INFORMATION: R or S
<220> FEATURE:
<221> NAME/KEY: MOD_RES
<222> LOCATION: (7)
<223> OTHER INFORMATION: S or Q
<220> FEATURE:
<221> NAME/KEY: MOD_RES
<222> LOCATION: (9)
<223> OTHER INFORMATION: V or Q
<220> FEATURE:
<221> NAME/KEY: MOD_RES
<222> LOCATION: (10)
<223> OTHER INFORMATION: I or V
```

-continued

```
<400> SEQUENCE: 3

Cys Gly Xaa Pro Ala Ile Xaa Pro Xaa Xaa Thr Gly Tyr
 1               5                  10

<210> SEQ ID NO 4
<211> LENGTH: 20
<212> TYPE: PRT
<213> ORGANISM: Gadus sp.
<220> FEATURE:
<221> NAME/KEY: MOD_RES
<222> LOCATION: (11)
<223> OTHER INFORMATION: S or T
<220> FEATURE:
<221> NAME/KEY: MOD_RES
<222> LOCATION: (13)
<223> OTHER INFORMATION: S, P or Y
<220> FEATURE:
<221> NAME/KEY: MOD_RES
<222> LOCATION: (20)
<223> OTHER INFORMATION: D or Q

<400> SEQUENCE: 4

Ile Val Asn Gly Glu Glu Ala Val Pro His Xaa Trp Xaa Trp Gln Val
 1               5                  10                  15

Ser Leu Gln Xaa
            20

<210> SEQ ID NO 5
<211> LENGTH: 13
<212> TYPE: PRT
<213> ORGANISM: Bovine sp.

<400> SEQUENCE: 5

Cys Gly Val Pro Ala Ile Gln Pro Val Leu Ser Gly Leu
 1               5                  10

<210> SEQ ID NO 6
<211> LENGTH: 20
<212> TYPE: PRT
<213> ORGANISM: Bovine sp.

<400> SEQUENCE: 6

Ile Val Asn Gly Glu Glu Ala Val Pro Gly Ser Trp Pro Trp Gln Val
 1               5                  10                  15
Ser Leu Gln Asp
            20

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Ala Ala Pro Phe
 1

<210> SEQ ID NO 8
<211> LENGTH: 225
<212> TYPE: PRT
<213> ORGANISM: Gadus sp.
<220> FEATURE:
<221> NAME/KEY: MOD_RES
<222> LOCATION: (9)
<223> OTHER INFORMATION: K or R
```

```
<220> FEATURE:
<221> NAME/KEY: MOD_RES
<222> LOCATION: (24)
<223> OTHER INFORMATION: Y or F
<220> FEATURE:
<221> NAME/KEY: MOD_RES
<222> LOCATION: (32)
<223> OTHER INFORMATION: K or E
<220> FEATURE:
<221> NAME/KEY: MOD_RES
<222> LOCATION: (33)
<223> OTHER INFORMATION: D or Q
<220> FEATURE:
<221> NAME/KEY: MOD_RES
<222> LOCATION: (64)
<223> OTHER INFORMATION: Y or F
<220> FEATURE:
<221> NAME/KEY: MOD_RES
<222> LOCATION: (71)
<223> OTHER INFORMATION: I or unknown
<220> FEATURE:
<221> NAME/KEY: MOD_RES
<222> LOCATION: (82)
<223> OTHER INFORMATION: N or D
<220> FEATURE:
<221> NAME/KEY: MOD_RES
<222> LOCATION: (92)
<223> OTHER INFORMATION: K or E
<220> FEATURE:
<221> NAME/KEY: MOD_RES
<222> LOCATION: (129)
<223> OTHER INFORMATION: A or D
<220> FEATURE:
<221> NAME/KEY: MOD_RES
<222> LOCATION: (136)
<223> OTHER INFORMATION: V or C
<220> FEATURE:
<221> NAME/KEY: MOD_RES
<222> LOCATION: (138)
<223> OTHER INFORMATION: N or S
<220> FEATURE:
<221> NAME/KEY: MOD_RES
<222> LOCATION: (204)
<223> OTHER INFORMATION: H or N
<220> FEATURE:
<221> NAME/KEY: MOD_RES
<222> LOCATION: (212)
<223> OTHER INFORMATION: M, V or C
<220> FEATURE:
<221> NAME/KEY: MOD_RES
<222> LOCATION: (224)
<223> OTHER INFORMATION: N or S

<400> SEQUENCE: 8

Ile Val Gly Gly Tyr Glu Cys Thr Xaa His Ser Gln Ala His Gln Val
 1               5                  10                  15

Ser Leu Asn Ser Gly Tyr His Xaa Cys Gly Gly Ser Leu Ile Asn Xaa
             20                  25                  30

Xaa Trp Val Val Ser Ala Ala His Cys Tyr Lys Ser Val Leu Arg Val
         35                  40                  45

Arg Leu Gly Glu His His Ile Arg Val Asn Glu Gly Thr Glu Gln Xaa
     50                  55                  60

Ile Ser Ser Ser Val Xaa Arg His Pro Asn Tyr Ser Ser Tyr Asn
65                  70                  75                  80

Ile Xaa Asn Asp Ile Met Leu Ile Lys Leu Thr Xaa Pro Ala Thr Leu
                 85                  90                  95

Asn Gln Tyr Val His Ala Val Ala Leu Pro Thr Glu Cys Ala Ala Asp
            100                 105                 110

Ala Thr Met Cys Thr Val Ser Gly Trp Gly Asn Thr Met Ser Ser Val
        115                 120                 125
```

-continued

```
Xaa Asp Gly Asp Lys Leu Gln Xaa Leu Xaa Leu Pro Ile Leu Ser His
    130             135         140

Ala Asp Cys Ala Asn Ser Tyr Gly Pro Gly Met Ile Thr Gln Ser Met
145             150             155                 160

Phe Cys Ala Gly Tyr Leu Glu Gly Gly Lys Asp Ser Cys Gln Gly Asp
            165             170                 175

Ser Gly Gly Pro Val Val Cys Asn Gly Val Leu Gln Gly Val Gly Val
        180             185             190

Val Ser Trp Gly Tyr Gly Cys Ala Glu Arg Asp Xaa Pro Gly Val Tyr
        195             200             205

Ala Lys Val Xaa Val Leu Ser Gly Trp Val Arg Asp Thr Met Ala Xaa
    210             215             220

Tyr
225
```

FISH SERINE PROTEINASE AND THEIR PHARMACEUTICAL AND COSMETIC USE

Figure 1:
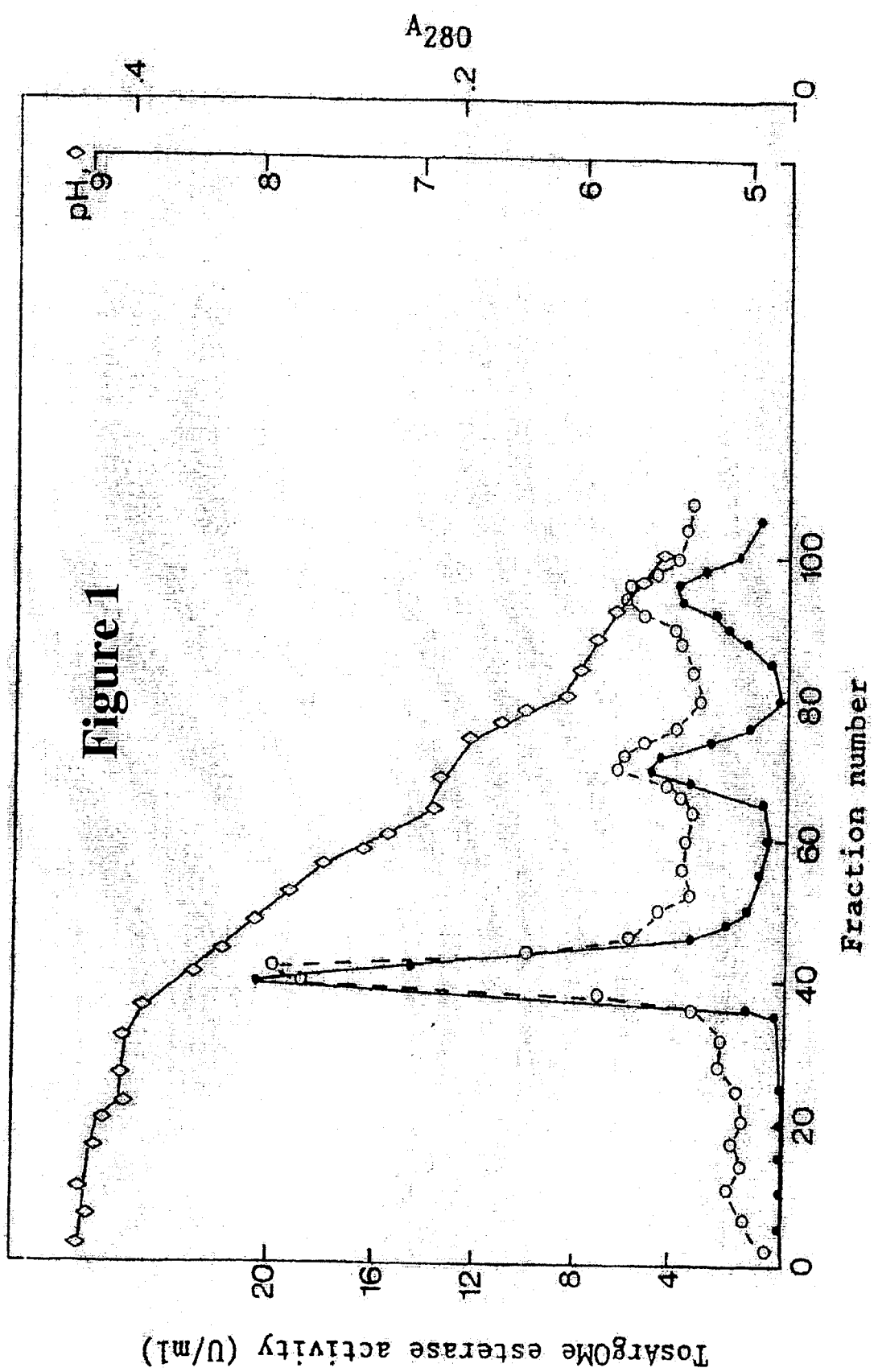

This application is a Division of prior U.S. application Ser. No. 09/411,688, filed Oct. 12, 1999, the contents of which are incorporated herein by reference. Priority is also claimed under 35 U.S.C. §§119/365 to application Ser. No 5086/99, filed in Iceland on Jun. 18, 1999, the contents of which are hereby incorporated herein by reference.

FIELD OF INVENTION

The present invention relates in its broadest aspect to the field of treatment and prevention of diseases and to the cosmetic field, in particular the pharmaceutical and cosmetic use of serine proteinases derived from fish. Specifically there are provided pharmaceutically or cosmetically active compositions comprising as an active component, trypsin and/or chymotrypsin isolated from Atlantic cod, and serine proteinases related to such enzymes.

TECHNICAL BACKGROUND AND PRIOR ART

U.S. Pat. Nos. 4,801,451 and 4,963,491 disclose a mixture of exo- and endopeptidases isolated from Antarctic krill (*Euphasia superba*) and the use of this mixture as a cleaning solution. U.S. Pat. No. 4,801,451 discloses the use of such enzymes to remove foreign matter and dead tissue from wounds. International patent application WO 85/04809 discloses the use of krill enzymes as a digestion promoting agent. EP-A1-0170115 discloses the use of krill enzymes to dissolve blood clots.

However, all of these references disclose impure or poorly characterized materials. A purified peptidase or mixture of purified peptidases is desirable to provide a pharmaceutically useful product. Furthermore, no disclosure is found wherein a purified peptidase or mixture of purified peptidases is useful for treating e.g. arthritis, inflamed joints, bursitis, osteoarthritis, rheumatoid arthritis, septic arthritis, phlebitis, eczema, rash, psoriasis or infectious diseases.

International patent application WO 96/24371 discloses the use of a krill-derived multifunctional proteolytic enzyme and a family of crustacean and fish derived proteolytic enzymes having substantial structural similarity to the multifunctional enzyme derived from Antarctic krill. This application also relates to methods of purifying the multifunctional enzyme and to pharmaceutical, cosmetic and other uses of the multifunctional enzyme. Substantial structural similarity to the multifunctional enzyme derived from Antarctic krill is defined in that application as at least 70% homology with the krill derived proteinase. The cod derived trypsin and chymotrypsin as disclosed herein have less than 70% homology with the krill derived multifunctional enzyme. Additionally, the cod derived trypsins and chymotrypsins are not multifunctional enzymes.

A major objective of the present invention is to provide the use of the cod derived trypsins and chymotrypsins in pharmaceutical compositions or medicaments for local and topical application to treat internal diseases and disorders and cosmetic use of such enzymes. Another objective of the present invention is the use of the cod derived trypsins and chymotrypsins for use in pharmaceutical compositions or medicaments for the transport of other proteineous or non-proteineous active compounds through the skin for local and topical application to treat internal diseases and disorders. It has been found that such serine proteinases are pharmaceutically highly active against a variety of diseases.

SUMMARY OF THE INVENTION

Accordingly, the present invention pertains in a first aspect to a fish serine proteinase for use as a medicament. In this context, particularly useful proteinases include trypsins and chymotrypsins derived from cod such as the Atlantic cod.

In a further aspect the invention relates to the use of a fish serine proteinase in the manufacturing of a medicament for treating and/or preventing a disease in a human or an animal. Diseases and disorders which may be treated or prevented include pain, acute inflammation, chronic inflammation, arthritis, inflamed joints, bursitis, osteoarthritis, rheumatoid arthritis, juvenile rheumatoid arthritis, septic arthritis, fibromyalgia, systemic lupus erythematosus, phlebitis, tendinitis, rash, psoriasis, acne, eczema, facial seborrheic eczema, eczema of the hands, face or neck, foreskin infections, athlete's foot, fistulae infections, infected topical ulcers, navel infections in newborns, wrinkels, scars, kelloids, boils, warts and allergic itch, hemorrhoids, wounds, wound infections, wounds from burns, a fungal infection and an immunogical disorder including an autoimmune disease.

In still further aspects, the invention provides the use of a fish serine proteinase in the manufacturing of a medicament for removing dead or peeling skin from otherwise healthy skin and the use of a fish serine proteinase in the manufacturing of a medicament for treating or preventing a disesease in whose pathogenesis a receptor-mediated binding is involved.

In yet further aspects, the invention relates to pharmaceutical and cosmetic compositions comprising a fish serine proteinase and to a method of treating and/or preventing a disease in a human or an animal, the method comprising administering to said human or animal a pharmaceutically effective amount of a fish serine proteinase.

In accordance with the invention there are also provided a method of preparing a purified preparation of cod trypsin isoenzymes, the method comprising the steps of (i) preparing an aqueous extract of cod viscera, (ii) subjecting the aqueous extract to a series of chromatography steps incuding at least one step using a cation exchange resin, at least one step using an anion exchange resin and as a last step a chromotography step using a p-aminobenzamidine affinity ligand, and (iii) desorbing and eluting the trypsin bound to the p-aminobenzamidine affinity ligand and a purified preparation of cod trypsin comprising, when it is subjected to SDS-PAGE electrophoresis and FPLC Mono Q chromatography as the only protein bands three bands of trypsin isoenzymes.

DETAILED DISCLOSURE OF THE INVENTION

The present invention provides the use of cod derived trypsins or other related trypsins or serine proteinases such as chymotrypsins derived from animals, in particular aquatic animals such as fish including cod, in a variety of medical and cosmetic contexts.

As used herein, the term "enzyme" is used to indicate an active enzyme if not otherwise specified. Also, as used herein the term "trypsin or other related peptidases" indicates peptidases of the trypsin type (EC 3.4.21.4) and all peptidases that have 90% or more sequence homology with the Atlantic cod trypsins (Ásgeirsson et al., Eur. J. Biochem. 180:85–94,1989; Gudmundsdottir et al., Eur. J. Biochem. 217:1091–1097, 1993). As used herein, the term "chymotrypsin or other related peptidases" means all peptidases of the chymotrypsin type (EC 3.4.21.1) and all peptidases that have 90% or more sequence homology with the Atlantic cod chymotrypsins A and B (Ásgeirsson and Bjarnason., Comp. Biochem. Physiol. 99B:327–335–94, 1991; Gudmundsdottir et al., Biochim ey Biophys. Acta 1219:211–214, 1994).

In particular, the enzymes according to the invention are useful for treating pain, inflammation, acute or chronic inflammation, arthritis, inflamed joints, bursitis, osteoarthritis, rheumatoid arthritis, juvenile rheumatoid arthritis, septic arthritis, fibromyalgia, systemic lupus erythematosus, phlebitis, eczema, rash, psoriasis, acne, wounds and candidiasis. In useful embodiments, cod trypsin or cod chymotrypsin or a mixture of these enzymes are administered locally and topically at the affected site in a pharmaceutical composition comprising the purified peptidase or mixture of purified peptidases and a pharmaceutically acceptable diluent or carrier, in particular but not limited to a hydrogel. In addition, the enzymes are useful for treating viral infections such as herpes outbreaks, fungal, bacterial or parasitic infections, including colitis, ulcers, hemorrhoids, corneal scarring, dental plaque and immune disorders including autoimmune disease.

Enzymes that are substantially structurally similar to the cod-derived trypsin and chymotrypsin enzymes have the same utility as the cod enzymes.

In particular, these trypsin and chymotrypsin enzymes are useful for treating arthritis, inflamed joints, bursitis, osteoarthritis, rheumatoid arthritis, juvenile rheumatoid arthritis, septic arthritis and phlebitis. In such treatments, the trypsin or chymotrypsin or a mixture of both enzymes are administered locally and topically at the site of arthritis or inflammation in a pharmaceutical composition comprising the trypsins or the chymotrypsins or both enzymes and a pharmaceutically acceptable diluent or carrier, in particular but not limited to hydrogel. In addition, the trypsin and chymotrypsin enzymes according to the invention are useful for treating viral infections such as herpes outbreaks, fungal, bacterial or parasitic infections, including colitis, ulcers, hemorrhoids, corneal scarring, dental plaque, acne, wounds, candidiasis and immune disorders including autoimmune disease.

In particular the invention relates to the medical, pharmaceutical and cosmetic uses of trypsilles derived from Atlantic cod or other animals. There are three trypsines of trypsin in Atlantic cod that have been purified and characterized. They have been termed Trypsin I, II, and III (Asgeirsson et al., Eur. J. Biochem. 180:85–94, 1989). The cod trypsins have the amino terminal sequence (SEQ ID NO:1) I-V-G-G-Y-Q/E-C-E/T-K/R-H-S-Q-A-H-QV-S-L-N-S while mammalian trypsins such as bovine tiypsin have the amino terminal sequence (SEQ ID NO:2) I-V-G-G-Y-T-C-G-A-N-T-V-P-Y-Q-V-S-L-N-S. All three isoforms of cod trypsin have a similar molecular mass of about 24 kDa.

The invention also relates to the medical, pharmaceutical and cosmetic uses of chymotrypsins derived from Atlantic cod or other animals. There are two major isoenzymes of chymotrypsin in Atlantic cod that have been purified and characterized. They have been designated Chymotrypsin A and B (Ásgirsson and Bjarnason., Comp. Biochem. Physiol. 99B:327–335–94, 1992). The cod chymotrypsins have the dual amino terminal sequences of one of its active forms C-G-R/S-P-A-I-S/Q-P-V/Q-I/V-T-G-Y (SEQ ID NQ:3) (A chain) and I-V-N-G-E-E-A-V-P-H-S/T-W-S/P/Y-W-Q-V-S-LQ-D/Q (SEQ ID NO:4) (B chain) whereas mammalian chymotrypsins such as bovine chymotrypsin A have the amino terminal sequences C-G-V-P-A-I-Q-P-V-L-S-G-L (SEQ ID NO:5) (A chain) and I-V-N-G-E-E-A-V-P-G-S-W-P-W-Q-V-S-L-Q-D (SEQ ID NO:6) (B chain). Both isoforms of cod chymotrypsin have a similar molecular mass of about 26 kDa.

Cod trypsins and chymotrypsins are isolated and purified from cod viscera except liver, spleen and roe. The enzymes are extracted from the whole or minced viscera by aqueous extraction with gentle stirring at any ratio of viscera to water, preferably a ratio (w/w) of from 1:1 to 1:10 of offal to water. After separation of the crude extract solution and residual offal, the extract is clarified by sedimentation or filtration. The clarified solution is concentrated preferably by ultrafiltration or ion exchange and then preferably microfiltered to achieve a true solution of low bioburden suitable for packed column chromatography that may include several steps. Subsequently, cod trypsin is purified by affinity chromatography preferably by amino benzamidine affinity chromatography and chymotrypsin by hydrophobic interaction chromatography preferably by Phenyl Sepharose chromatography.

The preferred method of application of the purified enzymes or mixture of purified enzymes 25 is in a preparation of hydrogel and water containing 0 to 85% (vol/vol) of a polyvalent alcohol (polyol) such as glycerol. A suitable concentration of chymotrypsin activity is 0.1 to 10,000 enzyme units of activity for CBZ-Gly-Pro-Arg-pNA (carbobenzoxy Gly-Pro-Arg-para nitroanalide) per 100 milliliters of the final hydrogel preparation and the appropriate concentration of chymotrypsin activity is 0.1 to 10,000 enzyme units of activity for Succinyl-Ala-Ala-Pro-Phe pNA (SEQ ID NQ:7) per 100 milliliters of the final hydrogel preparation.

The invention also provides a pharmaceutical composition comprising the cod trypsins and related peptidases and a pharmaceutically acceptable diluent or carrier.

The invention further provides (a) methods relating to certain conditions using effective amounts of the purified enzymes described above, (b) compositions or substances for use in such methods, (c) pharmaceutical compositions containing effective amounts of enzymes for use in such methods, and (d) uses of the enzyme or enzyme composition for manufacturing a medicament for use in such methods. The methods are for:

treating or prophylactically preventing an indication selected from the group consisting of pain, inflammation, acute or chronic inflammation, arthritis, inflamed joints, bursitis, osteoarthritis, rheumatoid arthritis, juvenile rheumatoid arthritis, septic arthritis, fibromyalgia, systemic lupus erythematosus and phlebitis where preferably the amount is treating or preventing effective amount;

treating or prophylactically preventing dermatological conditions such as e.g. acne, rash, psoriasis or eczema, including facial seborrheic eczema or eczema of the hands, face, scalp or neck, hemorrhoids and the like, where preferably the amount of the cod trypsins and related peptidases administered is a dermatological condition treating or preventing effective amount;

treating or prophylactically preventing wound infection and debriding wounds (by applying to the wound a microbial infection-preventing effective amount of the enzyme or by enhancing the healing of wounds by administering a microbe inhibiting effective amount of the enzyme), when treated the wound can be substantially free of necrotic tissue; removing dead or peeling skin from otherwise healthy skin to improve the skin's appearance, where preferably the amount of the enzyme administered is a dead skin removing effective amount;

treating or prophylactically preventing cystic fibrosis, cancer, e.g. by administering a tumor treating effective amount or a tumor metastasis preventing or inhibiting amount of enzyme, atherosclerosis, asthma, septic shock, toxic shock syndrome, tissue adhesions such as tendonsheath, abdominal post-surgical or joint adhesions, reperfusion injury, malaria, immune disorder such as an autoimmune disease, apoptosis, colitis and enteritis, such as Crohn's disease, where preferably the amount of the cod trypsins and related peptidases administered are effective for treating or preventing;

treating or prophylactically preventing a microbial infection, e.g. a viral infection such as a herpes virus infection (e.g. HSV-1, HSV-2, herpes zoster or genital herpes infection), HIV, hepatitis, influenza, coronavirus, cytomegalovirus, rhinovirus or papilloma virus infection; an infection causing a gastrointestinal disease such as ulcer or diarrhoea; a fungal infection such as systemic, skin, oral, vaginal or esophageal fungal infection, including e.g. yeast infection, including a fungal nail infection and *candida* infections; microbial infections of the eye, preferably treated with ocular administrations; bacterial infections including infection by *Staphylococcus* spp., *Streptococcus* spp., *Klebsiella* spp., *Pseudomonas* spp., *Neisseria gonorrheae*, *Haemophilus* spp., *Chlamydia* spp., syphilis and *E. coli* infections and bacterial infections causing chancroid; opportunistic microbial infections in immunocompromised patients where preferably the administered amount of the cod trypsins is a microbial infection-treating or -preventing effective amount or has inhibitory activity against cell-cell or cell-virus adhesion;

removing dental plaque, where preferably the amount of the enzyme administered is a dental plaque removing effective amount; and lysing blood clots, where preferably the amount of the enzyme is a clot lysing effective amount.

The method comprises administering a composition comprising the cod trypsins and/or chymotrypsins, or related peptidases as described above. The composition of the invention can also be used to remove dead or divergent cells.

The invention provides topical cosmetic and medical compositions comprising the purified cod trypsin, chymotrypsin or other related peptidases described above; and gel, cream or suppository composition.

The invention also provides (a) methods for treating or prophylactically preventing a cell-cell or cell-virus adhesion related syndrome, comprising administering an anti-adhesion effective amount of the cod trypsins or chymotrypsins or related peptidases effective to remove or inactivate a cellular or viral acceptor or receptor adhesion component that is involved in the cell-cell or cell-virus adhesion, (b) compositions or substances for use in such methods, (c) pharmaceutical compositions containing effective amounts of enzyme for use in such methods, and (d) uses of the enzyme composition for manufacturing a medicament for use in such methods. Generally, the syndrome involves inflammation, arthritis, inflamed joints, bursitis, osteoarthritis, rheumatoid arthritis, juvenile rheumatoid arthritis, septic arthritis, phlebitis, eczema, rash, psoriasis, acne, wounds, candidiasis and immune disorders including autoimmune diseases, shock, tumor metastasis, transplantation rejection reactions or microbial infections. Preferably, (a) the syndrome is selected from the group consisting of microbial infection, immune disorder, cystic fibrosis, atherosclerosis, cancer, asthma, septic shock, toxic shock syndrome, conjunctivitis, reperfusion injury and pain, and (b) a cell surface receptor, associated with the cell-cell or cell-virus adhesion syndrome, selected from following, which cod trypsin has been shown to cleave, consisting of CD4, CD8, CD54 (ICAM-1), CD31, CD62L, CD102 (ICAM-2), CD11a/CD18, is removed or inactivated by the administered enzyme. Preferably, a microbial infection is treated or prevented and the microbial infection is herpes, HIV, hepatitis or papilloma infection; an infection causing colitis or diarrhoea; a *Candida* infection, such as an oral, vaginal or esophageal *Candida* infection; a cold or influenza infection; a *Staphylococcus, Streptococcus, Klebsiella, Pseudomonas, Haemophilus* or *E. coli* infection; a primary or secondary infection of leprosy; or an infection causing conjunctivitis or tuberculosis.

In one embodiment, the invention provides a method of inhibiting or prophylactically preventing the transmission of a pathogenic microbe by administering the cod trypsin or chymotrypsin enzymes. Preferably, the cod trypsin and/or chymotrypsin enzyme is applied to the portion of the body that comprises the primary transmission entryway for the microbe in question. In one preferred embodiment, a spray, ointment or wash is applied to a body orifice involved in sexual activity, for instance, to prevent HIV or hepatitis transmission. In another preferred embodiment, the cod trypsin or related peptidases is applied to the upper airways, for example, via an aerosol, to inhibit or prevent the transmission of a common cold virus, such as a rhinovirus or a coronavirus.

In one aspect, the method of extra-corporeally treating a tissue, body fluid or composition of cells to remove cell adhesion components reduces the immune rejection of tissue, body fluid or composition of cells that is transplanted from one individual to another. In another aspect, such treatments remove or inactivate the cell adhesion components found in the treated tissue, body fluid or composition of cells involved in a microbial infection.

In treating or prophylactically preventing septic shock or toxic shock syndrome by administering the cod trypsins or related peptidases, appropriate routes of administration include systemic administration. For vaginal infections associated with shock, vaginal flushes, creams, gels or suppositories may be used as a method of administration.

In treating or prophylactically preventing pain, inflammation, acute or chronic inflammation, arthritis, inflamed joints, bursitis, osteoarthritis, rheumatoid arthritis, juvenile rheumatoid arthritis, septic arthritis, fibromyalgia, systemic lupus erythematosus, phlebitis by administering the cod trypsins or related peptidases, appropriate routes of administration would include without limitation creams, gels or suppositories, in particular but not limited to hydrogels containing glycerol or other polyols.

In treating or prophylactically preventing rash, psoriasis, acne, eczema, including facial seborrheic eczema or eczema of the hands, face, scalp or neck, foreskin infections, athlete's foot, fistulae infections, infected topical ulcers, navel infections in newborns, wrinkels, scars and kelloids, boils, warts and allergic itch, hemorrhoids and the like, wounds, wound infections, wounds from burns, removing dead or peeling skin from otherwise healthy skin to improve the skin's appearance, a fungal infection such as systemic, skin, oral, vaginal or esophageal fungal, including for example, yeast infection, including a fungal nail infection and *Candida* infections and immune disorders including autoimmune diseases by administering the cod trypsins, chymotrypsins or peptidases related to these enzymes, appropriate routes of administration would include creams, gels or suppositories, in particular but not limited to hydrogels containing glycerol or other polyols.

Accordingly, it is one objective of the present invention to provide a composition for the treatment of pain, inflammation, acute or chronic inflammation, arthritis, inflamed joints, bursitis, osteoarthritis, rheumatoid arthritis, juvenile rheumatoid arthritis, septic arthritis, fibromyalgia, systemic lupus erythematosus, phlebitis, rash, psoriasis, acne, eczema, including facial seborrheic eczema or eczema of the hands, face,scalp or neck, foreskin infections, athlete's foot, fistulae infections, infected topical ulcers, navel infections in newborns, wrinkles, scars and kelloids, boils, warts and allergic itch, hemorrhoids and the like, wounds, wound infections, wounds from burns, removing dead or peeling skin from otherwise healthy skin to improve the skin's appearance, a fungal infection such as systemic, skin, oral, vaginal or esophageal fungal infection including e.g. yeast infection, including a fungal nail infection and *Candida* spp. infections, and immune disorders including autoimmune diseases. Another object is to provide a method for the preparation of a composition to be used for the treatment of said diseases. A third object is to provide a method for the application of said composition for the treatment of said diseases, including dose levels for external and topical applications. The invention hence is based on compositions comprising enzymes where previously no enzymes have been used or a better enzyme where enzymes have been used.

The above objectives are achieved by using a composition containing an effective amount of the cod trypsins and/or chymotrypsins which is capable of relieving the pain, inflammation, arthritis, swelling, edema, psoriasis eczema, dermatitis, rash and/or other symptoms of the diseases mentioned in the introductory part. The cod enzymes can be obtained at a high yield and in a relatively simple manner from cod viscera. It has been found that the cod enzymes can be purified in a relatively straightforward manner with reasonable yields. The purified cod trypsin contains three major isozymes of the enzyme and cod chymotrypsin contains two major isozymes. One or all isozymes can be used for the purpose of the invention.

It has now been established that the cod trypsin and chymotrypsin enzymes of the invention effectively remove or inactivate certain cell-surface adhesion molecules, bacterial enterotoxins, cytokines, inflammatory mediators and matrix metalloproteinases (MMPs) such as CD4, CD8, CD54 (ICAM-1), CD31, CD62L, CD102 (ICAM-2), CD11a/CD18, TNF-alfa, IL-1, and MMP-9, without affecting the cell viability. This adhesion site cleavage or inactivation phenomenon of cytokines, inflammatory mediators and matrix metalloproteinases is believed to provide at least a partial explanation for the effectiveness of the cod trypsins and chymotrypsins against many, though probably not all, of the indications against which the cod trypsins and chymotrypsins are effective. Thus TNF-alpha is implicated in both arthritis, psoriasis, cancer and inflammation (See Cytokines, Eds. Mire-Slui and Thrope, Academic press, 1998, p 350).

The cod trypsins and chymotrypsins appear to be more effective than other conventional proteases in many respects. When a panel of 13 of the most active proteases in this respect were compared for activity towards 16 of the aforementioned certain cell-surface adhesion molecules, bacterial enterotoxins, cytokines, inflammatory mediators and MMPs, as well as their sensitivity to serum inhibition, the Atlantic cod trypsin and chymotrypsin were found to be far the most active. The proteases were scored 2 points for high to very high activity, 1 point for low to moderate activity and 0 point for very low to no activity (reverse scores for serum inhibitory activity for the proteases). On the basis of this scoring scheme the Atlantic cod trypsin scored 30 points and the Atlantic cod chymotrypsin scored 29 points, whereas the known krill multifunctional protease scored 16 points. The bovine trypsin and chymotrypsin proteases were found lacking in this respect. Furthermore, the cod trypsins and chymotrypsins are 2 to 20 fold more active than their bovine counterparts when conventional small chromogenic substrates are used to compare their activities (Ásgeirsson et al., Eur. J. Biochem. 180:85–94, 1989; Ásgeirsson and Bjarnason., Comp. Biochem. Physiol. 99B:327–335–94, 1991).

Cod viscera are useful sources for the cod trypsin and chymotrypsin enzymes of the invention. For instance, the enzymes can be extracted from frozen cod viscera as described above. The clarified and concentrated extract solution can be fractionated by ion exchange chromatography, preferably a first cation exchange chromatography step followed by an anion exchange chromatography step to bind and therby remove related serine proteases such as elastase and serine collagenases. In a subsequent and final step, cod trypsin is purified by affinity chromatography preferably using p-aminobenzamidine affinity column chromatography and chymotrypsin by hydrophobic interaction column chromatography preferably using Phenyl Sepahrose.

The cod trypsin used in the invention can be desorbed from the affinity matrix by applying conditions that will destabilize the interaction between the enzyme and the affinity ligand. Such conditions include high salt followed by low pH, preferably in 30% or more glycerol. The column eluent is allowed to flow into a neutralizing buffer to stabilize the cod trypsin after the acid elution step ( Ásgeirsson et al., Eur. J. Biochem. 180:85–94, 1989). The cod chymotrypsin used in the invention can be released from the Phenyl Sepharose column by applying conditions that will destabilize the interaction between the enzyme and the hydrophobic interaction ligand. Such conditions include high glycerol content in water or buffer, preferably 50% or more glycerol in water or buffer (Ásgeirsson and Bjarnason, Comp. Biochem. Physiol. 99B:327–335–94, 1991). By these methods the cod trypsin and chymotrypsin enzymes with a purity in excess of about 90% can be isolated. The cod trypsin fraction thus obtained contains 3 forms or isozymes of cod trypsin as manifested by SDS electrophoresis which yields one band, isoelectric focusing showing three bands and chromatofocusing chromatography which gives three peaks associated with the three trypsin isoforms (FIG. 1).

The serine proteases from other sources than Atlantic cod can be compared to the isolated Atlantic cod trypsin enzymes for molecular mass, isoelectric point, amino acid sequence, temperature or pH stability, temperature or pH maximum, proteolytic specificity and kinetic parameters, or for other properties of the Atlantic cod trypsin enzymes exemplified in the examples (Ásgeirsson et al., Eur. J. Biochem. 180:85–94, 1989). The activity of cod trypsin can be measured using tyrosine arginine methyl ester (TAME) as substrate. The isolated cod trypsin from the affinity column purification (90–100% purity) will preferably have specific activity of at least 140 U/mg at 25° C. and pH 8.1, as compared to 60 U/mg for the krill multifunctional hydrolase. Also, tryptic activity can be measured using Cbz-Gly-Pro-Arg-p-nitroanilide (Cbz-GPR-pNA) as substrate yielding a specific activity preferably at least about 100 U/mg. Furthermore, when Bz-Arg-pNA is used as substrate catalytic efficiency constants (kcat/Km) of 52, 20 and 7 s-1mM-1 are obtained for cod trypsin I, II and III respectively as compared to 3 s-1mM-1 for bovine trypsin (Ásgeirsson et al., Eur. J. Biochem. 180:85–94, 1989). Similar differences are seen for the cod chymotrypsins and bovine chymotrypsin (Ásgeirsson and Bjarnason, Comp. Biochem. Physiol. 99B:327–335, 1991).

The molecular mass of the cod trypsins is about 24 kDa, whereas their isoelectric points are 6.6, 6.2 and 5.5 for trypsin I, II and III respectively. The amino acid sequences of the three isozymes of cod trypsin can be expressed with the following sequence, (SEQ ID NO:8) which contains point variability due to the multiple isoforms:

```
I-V-G-G-Y-E-C-T-K/R-H-S-Q-A-H-Q-V-S-L-N-S-G-Y-H-Y/F-C-G-G-S-L-I-N-K/E-D/Q-W-V-V-
S-A-A-H-C-Y-K-S-V-L-R-V-R-L-G-E-H-H-I-R-V-N-E-G-T-E-Q-Y/F-I-S-S-S-S-V-I/X-R-H-P-N-
Y-S-S-Y-N-I-N/D-N-D-I-M-L-I-K-L-T-K/E-P-A-T-L-N-Q-Y-V-H-A-V-A-L-P-T-E-C-A-A-D-A-T-
M-C-T-V-S-G-W-G-N-T-M-S-S-V-A/D-D-G-D-K-L-Q-V/C-L-N/S-L-P-I-L-S-H-A-D-C-A-N-S-
Y-G-P-G-M-I-T-Q-S-M-F-C-A-G-Y-L-E-G-G-K-D-S-C-Q-G-D-S-G-G-P-V-V-C-N-G-V-L-Q-G-
V-G-V-V-S-W-G-Y-G-C-A-E-R-D-H/N-P-G-V-Y-A-K-V-M/V-C-V-L-S-G-W-V-R-D-T-M-A-N/S-Y,
``` wherein X is any amino acid or no amino acid, and cod trypsin I has amino acid resdue K in position 9, whereas cod trypsins II and III contain R in this position (Gudmundsdottir et al. 1993 and unpublished data).

Figure 2:
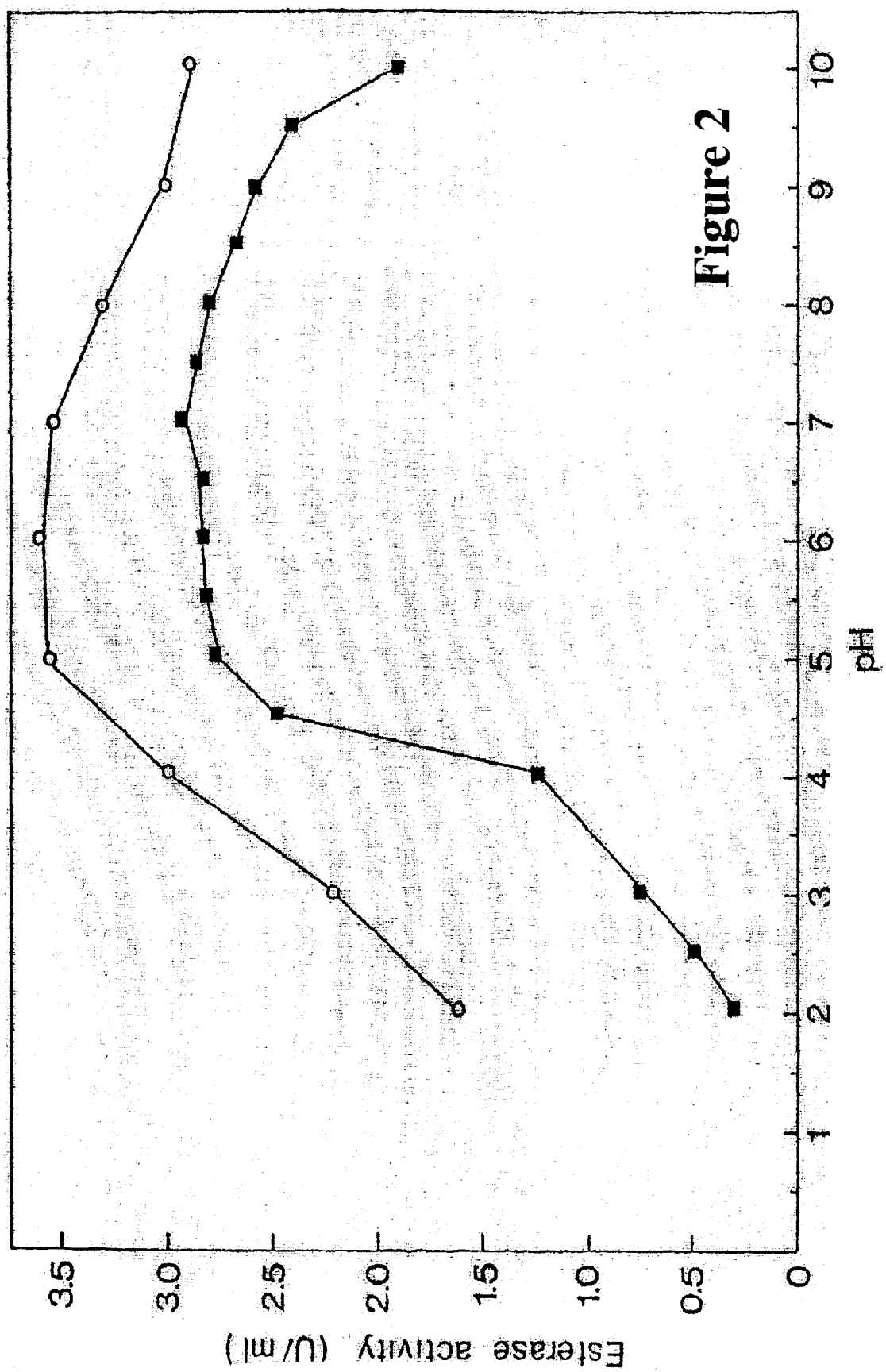

Generally, the cod trypsin isoenzymes will be sufficiently stable so that at least about 50% of the TAME activity is retained after incubation at 5° C. for 18 hours at pH 7.0 in a buffer solution containing 10 mM calcium chloride. However, only about 10% of the TAME activity is retained after incubation at 5° C. for 18 hours at pH 2.0 (FIG. 2).

Figure 3:
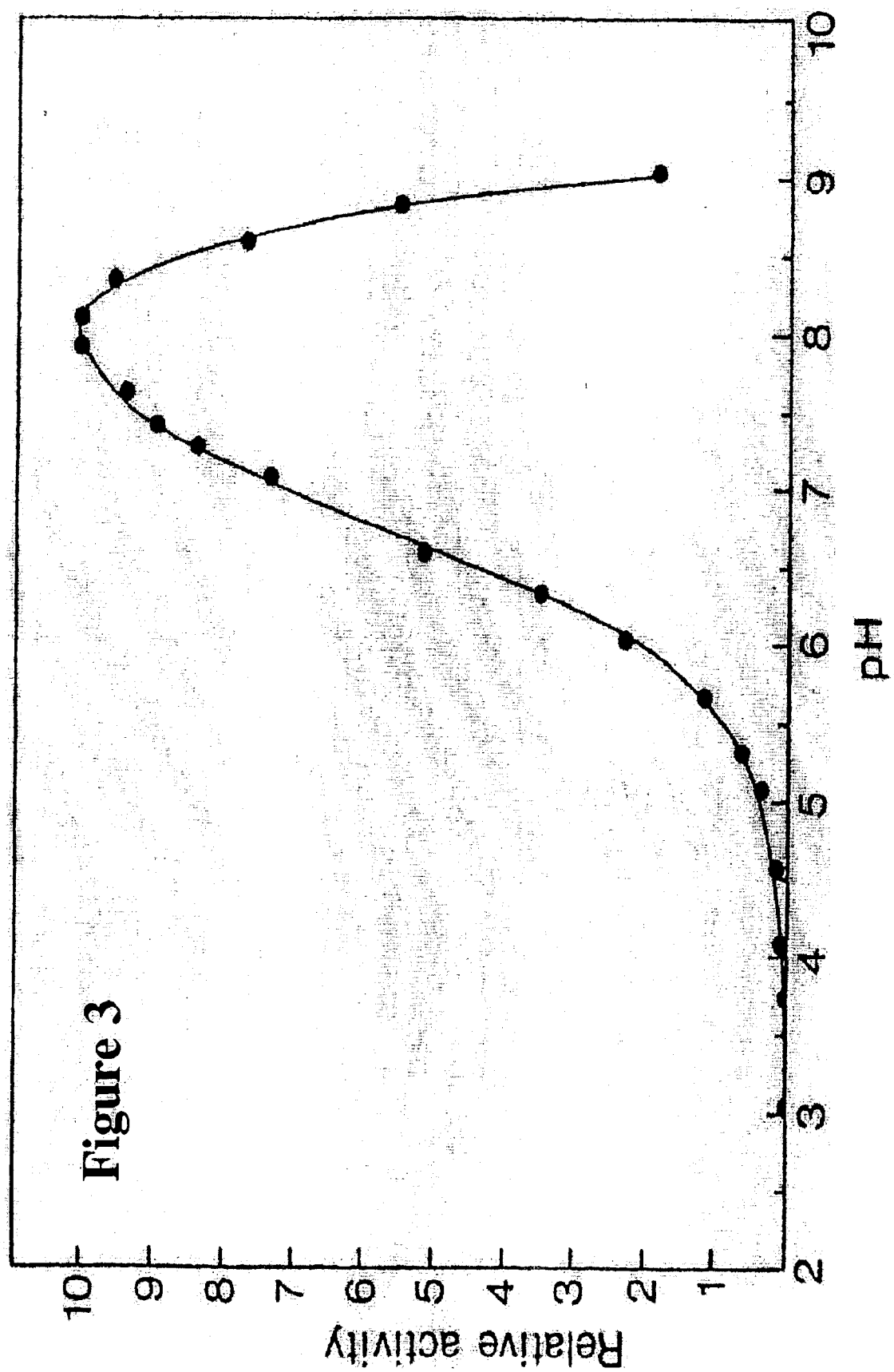
Figure 4:
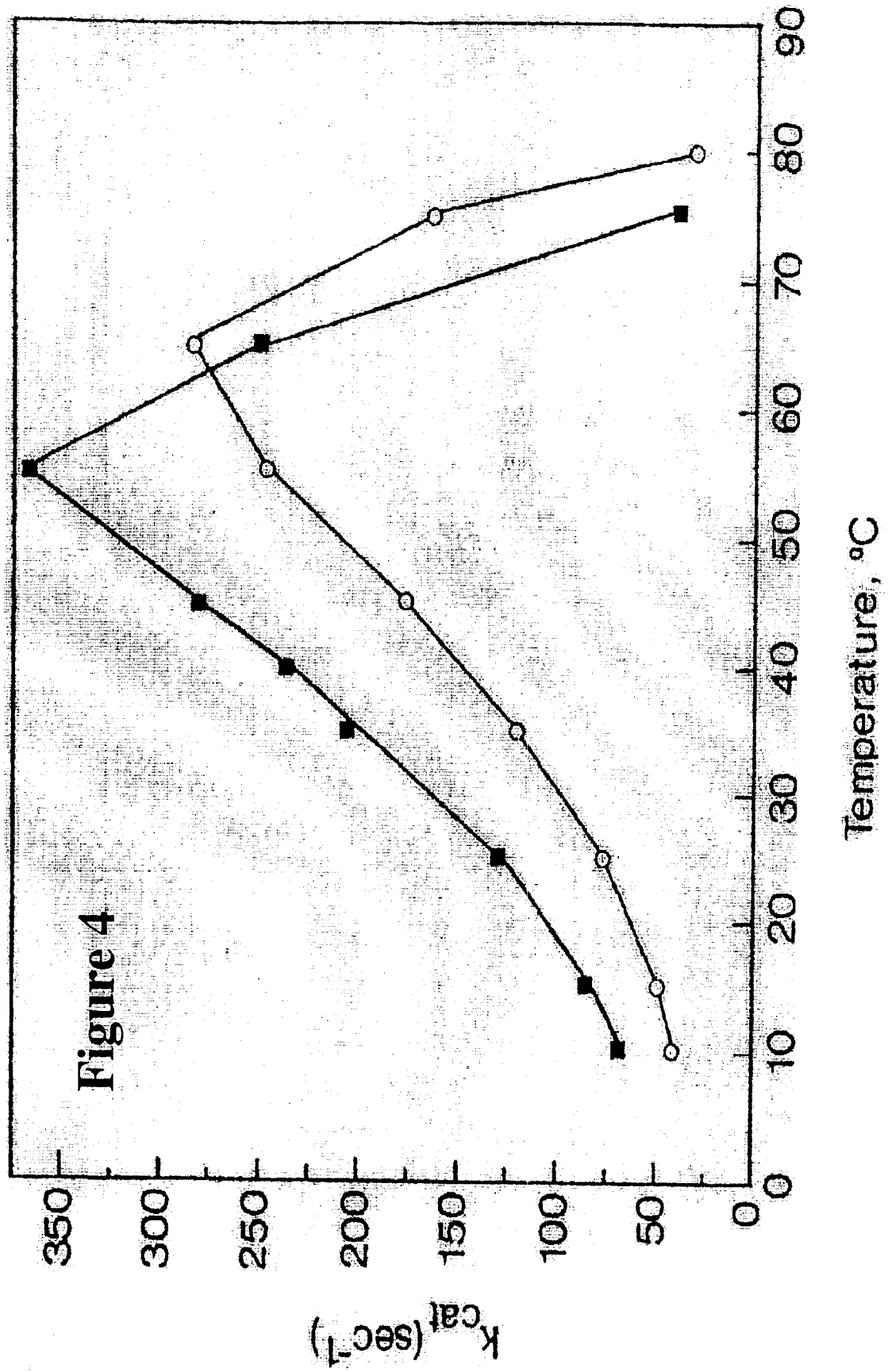

The pH optimum of the cod trypsins for TAME as substrate is preferably between about 7.0 and 8.7 more preferably about 8.0 (FIG. 3). Using TAME as the substrate, the Km at about pH 8.1 and 25° C. in the presence of 10 mM calcium chloride is preferably about 0.029 mM, 0.021 mM and 0.049 mM for cod trypsins I, II and III respectively. Preferably, cod trypsin has a temperature maximum of activity for TAME as substrate between 50 and 60° C. (FIG. 4).

The cod trypsin and chymotrypsin enzymes of the invention are administered topically, orally, rectally, vaginally, by instillation (for instance into the urinary tract or into fistulas), by the pulmonary route e.g. by use of an aerosol, by application of drops to the eye, or systemically, such as parenterally, including, for example, intramuscularly, subcutaneously, intraperitoneally, intraarterially or intravenously. The cod enzymes are administered in solution or combined with a pharmaceutically-acceptable carrier or excipient according to standard pharmaceutical practice. For the oral mode of administration, the cod enzymes are used in the form of tablets, capsules, lozenges, chewing gum, troches, powders, syrups, elixirs, aqueous solutions and suspensions, and the like. For parenteral administration, sterile solutions of the cod enzymes are usually prepared, and the pH values of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. For pulmonary administration, diluents and/or carriers will be selected to be appropriate to allow the formation of an aerosol. For topical administrations, the cod trypsin enzymes are typically administered in a hydrogel, containing 0 to 85% glycerol, such as about 20% to 30% glycerol and possibly up to 85% glycerol.

For topical treatments, a suitable dose of the cod trypsin enzymes per application ranges from about 0.01 $\mu g/cm^2$ to about 1 $mg/cm^2$, preferably from about 0.1 $\mu g/cm^2$ to about 0.01 $mg/cm^2$ (using e.g. about 0.01 mg/ml enzyme gel). For systematic treatments, dosages will generally be selected to maintain a serum level of the cod trypsin enzymes between about 0.1 mg/100 ml and about 100 mg/100 ml, preferably between about 0.5 mg/100 ml and about 2.0 mg/100 ml. In an alternative measure of preferred systematic administration amounts, preferably from about 0.1 mg/kg to about 10 mg/kg, more preferably about 1 mg/kg, will be used. For vaginal and urinary tract treatments, suitable flushing/instillation solutions of the cod trypsin enzymes will generally have concentrations from about 1 $\mu g/ml$ to about 15 mg/ml, preferably from about 100 $\mu g/ml$ to about 3 mg/ml. For all treatments, the enzyme composition will generally be applied from about 1 to about 10 times per day, preferably from about 2 to about 5 times per day. These values, of course, will vary with a number of factors including the type and severity of the disease, and the age, weight and medical condition of the patient, as will be recognized by those of ordinary skill in the medical arts. It is believed that substantially higher doses can be used without substantial adverse effect.

For wound healing, the cod trypsin enzymes are preferably applied more often than simply at the time at which the wound is first dressed. Preferably, the cod trypsin is applied at least about every time the wound dressing is changed. The cod trypsin enzymes can also be applied at least about every other day, more preferably, every day, or a few times per day. For dermatological situations such as eczema, psoriasis and the like, the cod trypsin and/or chymostrypsin enzyme hydrogel is preferably applied every day, more preferably twice per day. For acute or chronic inflammation, arthritis, inflamed joints, bursitis, osteoarthritis, and the like, the cod trypsin enzymes are preferably applied every day more preferably twice every day.

As illustrated in many of the clinical examples below, the cod enzyme hydrogel of the invention is effective to treat or prevent inflammatory conditions. Typically, inflammations are reduced to acceptable levels within 2 or 3 days from initiation of treatment. The examples also illustrate that the enzyme is effective to alleviate pain. Pain relief is often reported within 20 minutes to 2 hours of the start of treatment. Pain relief was not accompanied by loss of feeling in the treated tissue. More complete pain relief, such that the patient only suffered mild pain or a feeling of tenderness, was often experienced within 1 day of the start of treatment.

Generally, the cod enzymes according to the invention will be administered in an effective amount. An effective amount is an amount effective to either (1) reduce the symptoms of the disease sought to be treated, (2) induce a pharmacological change relevant to treating the disease sought to be treated, (3) inhibit or prevent infection or re-infection by an infective agent, or (4) prevent the occurrence of a non-infectious disease (for instance a disease treatable by blocking a cell adhesion phenomenon). For wound treatment, in one aspect, an effective amount includes an amount which, if regularly applied, prevents the occurrence of infection. In another aspect, for wound healing, an effective amount includes an amount effective to reduce the average time it takes for a wound to heal.

Numerous methods for determining percent homology of proteins are known in the art. One preferred method is to use version 6.0 of the GAP computer program for making sequence comparisons. The program is available from the University of Wisconsin Genetics Computer Group and utilizes the alignment method of Needleman and Wunsch, J. Mol. Biol. 48, 443 (1970) as revised by Smith and Waterman, Adv. Appl. Math., 2, 482 (1981). Another available method uses the FASTA computer program.

The invention will now be further illustrated in the following non-limiting examples and the drawings wherein FIG. 1. shows a chromatofocusing chromatograph of the Atlantic cod trypsin fraction off the aminobenzamidine affinity column purification step. The fraction eluted from the para aminobenzamidine column was gel filtered on a Sephadex G-25 column equilibrated in 25 mM monoethanolamine/acetic acid pH 9.4 containing 10 mM calcium chloride and subsequently applied to a column of PBE-94 ion exchange material (Pharmacia) equilibrated in the same buffer. The column was then eluted with Polybuffer 94 (adjusted to pH 5.5 with acetic acid) containing 10 mM calcium chloride. Activity for the substrate TAME (filled circles), absorbance at 280 nm (open circles) and pH (open diamonds) was monitored. The first eluted fraction was termed trypsin I, the second fraction trypsin II and the third fraction trypsin III;

FIG. 2. illustrates the effect of pH on the stability of Atlantic cod trypsin purified by para aminobenzamidine as measured by residual TAME activity after incubation at various pH values and two different time periods. The Atlantic cod trypsin samples were incubated at 5° C. for 30 minutes (open circles) and 18 hours (closed squares) at varying pH values. Residual activity for the substrate TAME was subsequently measured at pH 8.1 and 25° C.;

FIG. 3. shows the pH dependence of the activity of Atlantic cod trypsin purified by para aminobenzamidine as measured by using the TAME substrate. The buffers used at a final concentration 0.1 M were acetate (pH 3.0–5.9), hepes/HCl (pH 6.0–8.0) and glycinate (pH 8.3–9.0), all containing 10 mM calcium chloride; and FIG. 4 shows the temperature dependence of the activity of Atlantic cod trypsin I compared to the activity of bovine trypsin measured by using the TAME substrate. The enzymes were added to a preheated thermostated cuvette and after a short equilibration period the average rate of hydrolysis was determined during the following 3 minutes.

EXAMPLE 1

Preparation of a Mixture of Proteases from Cod

About 100 kg of frozen cod viscera were thawed and added to a four fold volume of cold potable water in an extraction tank and the pH adjusted to pH 8 to 9 with a sodium hydroxide solution. The mixture was stirred for about 2–6 hours at 0 to 5° C. After a brief period of crude sedimentation (about 30 minutes) the aqueous extract was run off the remaining insoluble viscera with a pump and collected in a sedimentation tank. The aqueous extract was allowed to stand in the cooled sedimentation tank to sediment for about 24 to 60 hours. The supernatant was decanted from the supernatant tank to a holding tank using a pump. The supernatant was concentrated 10 to 20 fold by ultrafiltration and diafiltered to an acceptable level of ionic strength with conductivity below about 3 mS/cm. About 10–15 liters of ultrafiltrated and diafiltered protein concentrate was obtained.

EXAMPLE 2

Purification of Cod Trypsin from Concentrated Cod Viscera Extract

About 10 liters of ultrafiltratered and diafiltered concentrate as obtained in Example 1 was applied to a continuous connected series of about 1 liter packed chromatography columns, the first containing a CM fast flow cation exchange resin (Pharmacia, Sweden), the second one a DEAE fast flow anion exchange resin (Pharmacia, Sweden) and the third one a p-aminobenzamidine affinity ligand coupled to a sepharose resin (Pharmacia, Sweden). The columns were pre-equilibrated with about 10 column volumes of 25 mM Tris buffer of pH 7.8, containing 2.5 mM calcium chloride (buffer A). The concentrate was pumped onto the columns at a flow rate of about 100 ml per minute. When the application of the concentrated solution onto the columns was completed, residual material was washed off the continuous column system with about 8 liters of buffer A.

After this wash was completed, the p-aminobenzamidine affinity column was disconnected from the other columns and washed with about 5 column volumes of a high salt solution of 25 mM Tris buffer pH 7.5 containing 0.5 M NaCl and 2.5 mM calcium chloride. The cod trypsins were then desorbed from the affinity ligand and eluted off the column with an acid solution of 25 mM acetic acid pH 3.2 containing 10 mM calcium chloride and 30% glycerol. The cod trypsin fraction was collected into a neutralizing buffer of 200 mM Tris pH 8.5 containing 30% glycerol.

The purified cod trypsin preparation was homogeneous by SDS PAGE electrophoresis and FPLC Mono Q chromatography and showed the three trypsin isozyme bands on isoelectric focusing. The enzyme preparation had a specific activity of about 100 U/mg using to Cbz-GPR-pNA as substrate as previously described. The purified preparation was filter sterilized through a 0.22 micron filter and stored frozen at about −20° C.

EXAMPLE 3

Preparation of a Hydrogel Preparation of Cod Trypsins

The purified cod trypsin preparation of Example 2 was mixed with hydrocolloid gel comprising an aqueous gel containing 0.8% w/v Carbomer 940, 30% glycerol and 0.08% paraoxybenzoate. The cod trypsin preparation was mixed in a 1:1 ratio with the hydrogel to give a final concentration of 1 enzyme unit per mg (U/mg) of the final gel-enzyme mixture (the enzyme hydrogel ointment), the enzyme unit being determined using Cbz-GPR-pNA as substrate as previously described. Thus, the resulting enzyme hydrogel ointment contained about 0.01 mg/ml, or 1 U/ml of the cod trypsin enzymes, 0.4% Carbomer 940, 20% glycerol and 0.04% paraoxybenzoate. In the following, this enzyme hydrogel ointment is referred to as Penzyme 100.

EXAMPLE 4

Treating Osteoarthritis With Penzyme 100

Seventeen individuals with osteoarthtitis, some with acute or very severe symptoms, were treated with the enzyme hydrogel ointment (Penzyme 100) of Example 3. The enzyme gel was applied once to twice per day, always once in the evening before retiring to bed and in most cases also in the morning. About 5 milliliters of the enzyme gel was applied on each affected area, such as each knee or hip or both hands. Larger quantities may be applied in severe cases. The gel was left to dry for about 10 to 30 minutes, depending on the amount applied, time available and the needs and requirements of the patient. This drying can be accelerated by the use of an air blowing device such as a hair dryer. All these patients experienced relief from symptoms within one week, most of them within 2 to 4 days. Patient No. 71 was unable to walk stairs before treatment but has had no problems doing so after treatment. These results are summarized in the following Table 4.1:

TABLE 4.1

Treating osteoarthritis with Penzyme 100

| Patient No. | Sex-age | Affected area | Applications per day | Relief after |
|---|---|---|---|---|
| 1 | F-67 | Knees, hands | 1–2 | 2 days |
| 4 | M-74 | Knees | 1–2 | 3 days |
| 17 | M-54 | Knees | 1 | 4 days |
| 19 | M-55 | Knees | 2 | 3 days |
| 21 | F-73 | Hips | 2 | 2 days |
| 30 | F-77 | Knees | 2 | 3 days |
| 36 | F-68 | Knees, hips | 2 | 3 days |
| 51 | F-63 | Hips | 2 | 3 days |
| 53 | F-75 | Knees, hips | 1–2 | 3 days |
| 54 | F-73 | Knees | 1–2 | 4 days |
| 55 | M-67 | Injured knee | 1 | 4 days |
| 65 | F-37 | Knees, hands | 2 | 3 days |
| 67 | F-72 | Knees | 1–2 | 4 days |
| 71 | F-78 | Knees, back | 2 | 3 days |
| 72 | M-54 | Hands | 1 | 2 days |
| 73 | F-76 | Hands, hips | 1–2 | 3 days |
| 77 | M-75 | Hips, feet, back | 1–2 | 3 days |

A few of the patients (Nos. 19 and 21) have been able to discontinue treatment and thus appear to have enjoyed permanent or long term relief from the disease, but most of them keep the symptoms under control with constant or intermittent use of Penzyme 100.

EXAMPLE 5

Treatment of Patients Suffering from Tendinitis

Eight individuals with tendinitis, some with very severe symptoms causing problems with sleep at night, were treated with the enzyme hydrogel ointment (Penzyme 100) of Example 3. The enzyme gel was applied topically on the affected area once to twice per day, about 5 to 10 milliliters on each affected area, depending on the size of the area. The gel was left to dry for about 10 to 30 minutes, depending on the amount applied, time available and the needs and requirements of the patient. All these patients experienced relief from symptoms with in two weeks, most of them within 2 to 4 days but others took longer, especially those with tendinitis of the elbow (tennis elbow or golfer's elbow). These results are summarized in the following Table 5.1:

TABLE 5.1

Treatment of patients suffering from tendinitis

| Patient No. | Sex-age | Affected area | Applications per day | Relief after |
|---|---|---|---|---|
| 15 | F-45 | Shoulders | 2 | 2 days |
| 37 | F-50 | Shoulders, arm | 2 | 2 days |
| 57 | F-55 | Shoulders | 1–2 | 4 days |
| 79 | F-43 | Shoulders | 2 | 2 days |
| 47 | M-63 | Golfer's elbow | 1 | 2 weeks |
| 49 | M-34 | Tennis elbow | 1 | 1 week |
| 84 | F-33 | Tennis elbow | 2 | 2 days |
| 20 | M-24 | Jumper's knee | 2 | 3 days |

All these patients have enjoyed permanent relief from the condition and have discontinued treatment.

EXAMPLE 6

Treatment of Fibromyalgia

Two patients suffering from severe fibromyalgia were treated with the enzyme hydrogel ointment (Penzyme 100) of Example 3. The enzyme gel was applied topically on the affected area twice per day, about 5 to 10 milliliters on each affected area, depending on size of the area. The gel was left to dry for about 10 to 30 minutes, depending on the amount applied, time available and the needs and requirements of the patient. Both patients (No. 78, F-50 and No. 92, F-53) experienced relief from symptoms within three weeks. Both use the enzyme gel treatment when pain reappears.

EXAMPLE 7

Treatment of Rheumatoid Arthritis

Five patients with rheumatoid arthritis, some with very severe symptoms, were treated with the enzyme hydrogel ointment (Penzyme 100) of Example 3. The enzyme gel was applied topically on the affected area usually at least twice per day, about 3 to 5 milliliters on each affected area, depending on the size of the area. The gel was left to dry for about 15 minutes, depending on the thickness of the gel applied. This drying period can be shortened by the use of an air blowing device such as a hair dryer. All five patients experienced relief from symptoms within 5 days. These results are summarized in the following Table 7.1:

TABLE 7.1

Treatment of rheumatoid arthritis

| Patient No. | Sex-age | Affected area | Applications per day | Relief after |
|---|---|---|---|---|
| 14 | M-55 | Hands | 1 | 5 days |
| 61 | F-47 | Hips, hands | 3 | 4 days |
| 65 | F-37 | Neck, hands | 2 | 2 days |
| 78 | F-50 | Neck, hands | 2 | 2 days |
| 94 | M-36 | Hands, chest | 1 | 3 days |

Patient No. 61 could not get out of bed in the morning and dress without assistance before she began the treatment, but was fully capable of doing so on her own after treatment. Patient No. 94 had pain in the, chest when breathing due to a complication of pleural effusion. She was relieved from these symptoms after 3 days of treatment with Penzyme 100. All of these patients keep the symptoms under control with constant or intermittent use of the enzyme gel treatment.

EXAMPLE 8

Treatment of Phlebitis

Five patients with various forms of phlebitis, such as thrombophlebitis, phlebothrombosis, chronic postphlebitic syndrome and varicose veins, in all cases in the calfs, some with very severe symptoms causing pain with difficulty of sleep, were treated with the enzyme hydrogel ointment (Penzyme 100) of Example 3. The enzyme gel was applied topically on the calf at least once per day, i.e. in the evening and in some cases also in the morning, about 5 milliliters on each calf. The gel is left to dry for about 15 minutes. All five patients experienced relief from symptoms within a few weeks. These results are summarized in the following table 8.1:

TABLE 8.1

Treatment of phlebitis

| Patient No. | Sex-age | Affected area | Applications per day | Relief after |
|---|---|---|---|---|
| 2 | F-69 | Leg | 1–2 | 3 weeks |
| 28 | M-54 | Calf | 1 | 2 weeks |
| 56 | M-71 | Calf | 1–2 | 2 weeks |
| 59 | F-59 | Calf | 1 | 2 weeks |
| 68 | F-72 | Calf | 1–2 | 4–5 days |

Patient No. 2 was diagnosed with chronic postphlebtic syndrome. Patient No. 68 does not sleep properly at night due to pain if she does not apply the gel before bedtime. All of these patients keep the symptoms under control with constant or intermittent use of the enzyme gel treatment.

EXAMPLE 9

Treatment of Psoriasis

Six patients with psoriasis, some chronic cases with very severe symptoms, were treated with the enzyme hydrogel of Example 3, but in the majority of the cases of psoriasis a hydrogel composition designated Penzyme 200 with double the cod trypsin concentration or 2 U/ml was used, since Penzyme 100 (1 U/ml cod trypsin) yielded rather slow and in some cases uncertain results. Patients claimed great improvements in treatment with the gel containing the higher cod trypsin content (Penzyme 200) as compared with the gel containing the lower trypsin content (Penzyme 100). A combination of cod trypsin and cod chymotrypsin, with a concentration of 1 U/ml of each enzyme, designated Penzyme 200-C, was also tested, and gave similar positive results as Penzyme 200. The enzyme gel was applied once to twice per day, always once in the evening before bedtime, after which the enzyme gel was left on the skin overnight and in some cases also in the morning after bathing and before dressing. The gel is applied as a thin layer or film and takes about 5 minutes to dry. All six patients experienced relief from symptoms within two weeks. The treatment was in some cases supplemented with conventional self-help methods such as sun bathing or UV light treatment. The results are summarised in the following Table 9.1:

TABLE 9.1

Treatment of psoriasis

| Patient No. | Sex-age | Gel type | Applications per day | Relief after |
|---|---|---|---|---|
| 3 | F-45 | Penzyme 200 | 1–2 | 4–5 days |
| 7 | M-63 | Penzyme 100 | 1–2 | 2 weeks |
| 18 | M-55 | Penzyme 100 | 1–2 | 1 week |
| 69 | M-29 | Penzyme 200 | 1–2 | 1 week |
| 86 | F-30 | Penzyme 200 | 1–2 | 1 week |
| 88 | M-21 | Penzyme 200 | 1–2 | 1 week |

Patient No. 3 has suffered from chronic and very severe psoriasis since the age of 5. She has tried all available treatments with limited results. The treatment with Penzyme 200 has yielded the only long term relief from symptoms for her. She claims that relief from symptoms is noticeable after about 4 days and total relief is accomplished within 2 to 3 weeks of treatment with one application per day before bed time.

Patient No. 69, also with severe chronic psoriasis, has experienced the permanent disappearance of some spots. All of these patients keep the symptoms under control with constant or intermittent enzyme gel treatment.

EXAMPLE 10

Treatment of Acne and Boils

Two individuals (patient Nos. 25, F-16 and no. 63, M-17) suffering from acne and one suffering from boils (No. 64, M-22) were treated with the cod trypsin hydrogel ointment (Penzyme 100) of Example 3. The enzyme gel was applied topically on the affected area (face) once per day, about 5 milliliters each time. The gel is left to dry for about 15 minutes after which it is left on the skin. All three individuals experienced total relief from symptoms within two weeks, and only used the enzyme gel treatment occasionally when symptoms started to reappear.

EXAMPLE 11

Treatment of Eczema, Dermatitis and Other Skin Conditions

Eighteen patients suffering from eczema, dermatitis and various other skin conditions, were treated with the cod trypsin hydrogel ointment (Penzyme 100) of Example 3. The enzyme gel was applied once per day (occasionally twice), usually in the evening before retiring to bed. The gel was applied as a thin layer or film. Drying occurred after about 5–10 minutes. A higher amount may be applied in severe cases. This drying can be accelerated by the use of an air blowing device such as a hair dryer. All these patients experienced relief from symptoms within one week, most of them in 2 to 4 days. The results are summarised in the following Table 11.1:

TABLE 11.1

Treatment of eczema, dermatitis and other skin conditions

| Patient No. | Sex-age | Condition, area | Applications per day | Relief after |
|---|---|---|---|---|
| 32 | M-24 | Seborrheic, hair | 1 | 2–3 days |
| 45 | M-23 | Seborrheic, hair | 1 | 3–4 days |
| 23 | F-26 | Dyshidrosis, palm | 2 | 7 days |
| 40 | F-21 | Dyshidrosis, palm | 1 | 4 days |
| 41 | F-45 | Dyshidrosis, palm | 2 | 3 days |
| 48 | F-33 | Dyshidrosis, sole | 1 | 2 weeks |
| 66 | F-40 | Hives, face | 1 | 2 days |
| 50 | F-25 | Paronychia, nails | 2 | 5 days |
| 20 | M-2 | Impetigo, mouth | 2 | 5 days |
| 11 | M-50 | Irritant derm, face | 2 | 2–3 days |
| 98 | F-52 | Irritant derm, face | 2 | 2–3 days |
| 12 | M-2 | Infantile eczema | 1 | 6 days |
| 46 | F-5 | Infantile eczema | 1 | 5 days |
| 87 | F-7 | Infantile eczema | 1 | 5 days |
| 99 | M-2 | Infantile eczema | 1 | 8 days |
| 97 | F-52 | Rosacea, face | 2 | 5–6 days |
| 100 | F-69 | Shingels, face | 2 | 2 days |
| 101 | F-47 | Discoid lupus | 2 | 7 days |

Some of the patients (Nos. 40, 41, 48, 66, 50, 20, 46, 87, 97, 100) have been able to discontinue treatment and thus appear to have enjoyed permanent or long term relief from the disease, but others keep the symptoms under control with constant or intermittent use of Penzyme 100.

EXAMPLE 12

Wound Healing

Two individuals (patient Nos. 44, M-4 and 85, M-9) with burns were treated with the cod trypsin hydrogel ointment (Penzyme 100) of Example 3. Two other patients (No. 62, F-47 and 96, M-70) were treated for post-operational wounds that would not heal. The enzyme gel was applied topically on the wounds at least twice per day and left on the affected area. All four individuals experienced good and complication free healing of their wounds within one to three weeks.

EXAMPLE 13

Treatments With Cod Chymotrypsin

For each of examples 4–12, the cod trypsin enzyme hydrogel is substituted with a cod chymotrypsin enzyme hydrogel or a hydrogel containing a mixture of cod trypsin and cod chymotrypsin.

What is claimed is:

1. A method of treating a disease selected from the group consisting of arthritis, tendinitis, phlebitis, psoriasis, acne, eczema, dermatitis, and wounds in a human or animal, the method comprising administering to said human or animal a pharmaceutically effective amount of a serine proteinase obtained from Atlantic cod.

2. The method according to claim 1, wherein the proteinase is a trypsin.

3. The method according to claim 2, wherein the trypsin is selected from the group consisting of tiypsin I, trypsin II and trypsin III.

4. The method according to claim 1, wherein the proteinase is administered topically.

5. The method according to claim 1, wherein the proteinase is administered gastroenterally.

6. A method of removing dead or peeling skin from otherwise healthy skin, comprising administering a pharmaceutically effective amount of a serine proteinase obtained from Atlantic cod.

7. The method according to claim 6, wherein the proteinase is a trypsin.

8. The method according to claim 7, wherein the trypsin is selected from the group consisting of trypsin I, trypsin II and trypsin III.

9. The method according to claim 6, wherein the proteinase is not multifunctional.

10. The method according to claim 6, wherein the proteinase is administered topically.

* * * * *